United States Patent
Wilkinson et al.

(10) Patent No.: US 8,225,644 B2
(45) Date of Patent: Jul. 24, 2012

(54) RHEOMETER WITH MODULAR ENVIRONMENTAL CONTROL SYSTEM

(75) Inventors: John Paul Wilkinson, Gloucester (GB); Joanne Elizabeth Langridge, Barnwood (GB); Justin Titus Tun, Birmingham (GB); James Francis Thomas, Telford (GB)

(73) Assignee: Malvern International, Ltd., Malvern, Worcestershire (GB)

( * ) Notice: Subject to any disclaimer, the term of this patent is extended or adjusted under 35 U.S.C. 154(b) by 538 days.

(21) Appl. No.: 12/462,337

(22) Filed: Jul. 31, 2009

(65) Prior Publication Data

US 2010/0186485 A1    Jul. 29, 2010

Related U.S. Application Data

(60) Provisional application No. 61/137,639, filed on Aug. 1, 2008.

(51) Int. Cl.
*G01N 11/14* (2006.01)

(52) U.S. Cl. .......... 73/54.28

(58) Field of Classification Search ....... 73/54.23–54.35
See application file for complete search history.

(56) References Cited

U.S. PATENT DOCUMENTS
6,588,254 B1 * 7/2003 Foster et al. ............ 73/54.23

FOREIGN PATENT DOCUMENTS
DE    102005042373    * 11/2006

* cited by examiner

*Primary Examiner* — Hezron E Williams
*Assistant Examiner* — Nathaniel Kolb
(74) *Attorney, Agent, or Firm* — Kristofer E. Elbing

(57) ABSTRACT

A rheometer uses a removable integrated environmental control cartridge that includes at least one environmental control unit, at least one supply port operative to interact with the supply port for a chassis of the rheometer. It also includes at least one mechanical alignment interface that is operative to interact with the mechanical alignment interface of the chassis to align both the mobile part with respect to the fixed part and the chassis supply port with respect to the environmental control cartridge part. In another general aspect, a rheometer can use an environmental control cartridge interface operative to report an identity of the integrated environmental control cartridge to an environmental control cartridge identification interface of its chassis.

31 Claims, 3 Drawing Sheets

RHEOMETER WITH MODULAR ENVIRONMENTAL CONTROL SYSTEM

CROSS-REFERENCE TO RELATED APPLICATION

This application claims the benefit of U.S. Provisional Application No. 61/137,639, filed Aug. 1, 2008, which is herein incorporated by reference.

FIELD OF THE INVENTION

This invention relates to rheometers, including rheometers with removable environmental control modules.

BACKGROUND OF THE INVENTION

Rheology is the study of flow and deformation of materials. It is important to control the external factors that affect a material while it is being rheologically tested, in order to correctly attribute resulting phenomena. External factors that may need to be controlled include, but aren't limited to, temperature, light sources, and energy fields.

It is important to control temperature accurately, whether it is to be provided isothermally or in a ramp. Some materials show changes in modulus (stiffness) as large as 20%/1° C. And some rheological phenomena are also attributable to external influences such as, but not exclusively, various wavelengths of light, external energy fields and pressure. Not all of these can be or are required to be controlled at once, which can result in the use of multiple types of environmental controller based on the requirements of a sample under test.

But changing between different environmental controllers tends to be quite difficult in current rheometer instrumentation. Typically, users must mechanically align top and bottom parts, and then set up a series of electrical and fluid connections.

SUMMARY OF THE INVENTION

In one general aspect, the invention features a rheometer for measuring properties of a sample that includes a mobile part having a contact surface for contacting the sample and a fixed part having a contact surface for contacting the sample. The rheometer also includes a vertical actuator for providing relative vertical motion between the mobile part and the fixed part, a rotary actuator for providing relative rotary motion between the mobile part and the fixed part, and a chassis operative to support the actuator, with an environmental control cartridge interface that includes at least one supply port and one mechanical alignment interface. A removable integrated environmental control cartridge includes at least one environmental control unit, at least one supply port operative to interact with the supply port for the chassis, and at least one mechanical alignment interface that is operative to interact with the mechanical alignment interface of the chassis to align both the mobile part with respect to the fixed part and the chassis supply port with respect to the environmental control cartridge part.

In preferred embodiments, the mechanical alignment interface for the chassis, the supply port for the chassis, the mechanical alignment interface for the environmental control cartridge, and the supply port for the environmental control cartridge can be positioned to cause the mechanical alignment interfaces and the supply ports to both engage each other, respectively, at substantially a same predetermined cartridge insertion position. The supply ports can be electrical supply ports. The electrical supply ports can be operative to supply control signals to and from the integrated environmental control cartridge. The electrical supply ports can be operative to supply identification signals from the integrated environmental control cartridge. The electrical supply ports can be operative to supply electrical power to the integrated environmental control cartridge. The electrical supply ports can be operative to supply control signals to and from the integrated environmental control cartridge, to supply identification signals from the integrated environmental control cartridge, and to supply electrical power to the integrated environmental control cartridge. The supply ports can be fluid circulation ports. The supply ports can be are environmental fluid circulation ports. The supply ports can be gaseous material circulation ports. The rheometer can further include a fluid conveyance control device outside of the environmental control cartridge that controls the conveyance of fluid through the fluid supply port of the chassis and further including disabling logic operative to disable the fluid conveyance control device when an integrated environmental control cartridge is removed. The supply ports can be compound electrical and cooling supply ports. Electrical and cooling portions of the supply ports can be positioned on the environmental control cartridge and on the chassis to simultaneously engage with their respective counterparts upon insertion. The rheometer can further include hot-swappable control logic operative to allow the integrated environmental control cartridge to be exchanged even while the chassis is powered up. The supply port can include at least one self-actuating connector. The fixed part can be integrated into the integrated environmental control cartridge. The mechanical alignment interfaces can be operative to constrain at least a portion of the integrated environmental control cartridge in three dimensions with respect to the moveable part. The mechanical alignment interfaces can be operative to constrain at least a portion of the integrated environmental control cartridge in three dimensions with respect to the moveable part. The mechanical alignment interface can be based on a kinematic alignment mechanism that provides a positioning reproducibility of within about +/− ten microns in all three dimensions. The mechanical alignment interfaces can be based on a cam. The mechanical alignment interfaces can be based on a dovetailed disk and a v-block. The environmental control cartridge can be inserted horizontally and the mechanical alignment interfaces can be based on a horizontally mounted dovetailed disk and a horizontally mounted v-block. A position of the v-block can be adjustable to allow the environmental control cartridge's position to be adjusted to a chassis-independent standard position. Each of the mechanical alignment interfaces can provide for an individual adjustment to allow the environmental control cartridge's position to be adjusted to a chassis-independent standard position. The alignment interfaces can each be compound interfaces that provide a first alignment interface portion to align the environmental control cartridge with respect to the mobile part and a second alignment interface portion to align the supply ports. The second alignment portion can include a loosely sprung mount for the chassis supply port. The second alignment portion can include a loosely fitting guide post.

In another general aspect, the invention features a rheometer for measuring properties of a sample that includes a mobile part having a contact surface for contacting the sample, a fixed part having a contact surface for contacting the sample, a vertical actuator for providing relative vertical motion between the mobile part and the fixed part, and a rotary actuator for providing relative rotary motion between the mobile part and the fixed part. The rheometer also includes a chassis operative to support the actuator, and including an environmental control cartridge interface including at least one cartridge identification interface, and a removable integrated environmental control cartridge including at least one environmental control unit, and at least one cartridge identification interface operative to report an identity of the integrated environmental control cartridge to the environmental control cartridge identification interface of the chassis. In preferred embodiments, the environmental control cartridge identification interfaces can each include one or more electrical connectors.

In a further general aspect, the invention features a method of operating a rheometer that includes receiving an environmental control cartridge, aligning the environmental control cartridge with respect to a mobile part of the rheometer, aligning a supply port on the environmental control cartridge with respect to a supply port on a chassis of the rheometer, and engaging the aligned supply ports. In preferred embodiments, both of the steps of aligning and the step of engaging can all take place substantially simultaneously.

Systems according to the invention can be advantageous in that they allow users to quickly change the configuration of a rheometer while maintaining highly accurate alignment. The use of self-identifying interchangeable cartridges can further simplify the task of changing rheometer configuration

DETAILED DESCRIPTION OF AN ILLUSTRATIVE EMBODIMENT

Figure 1:
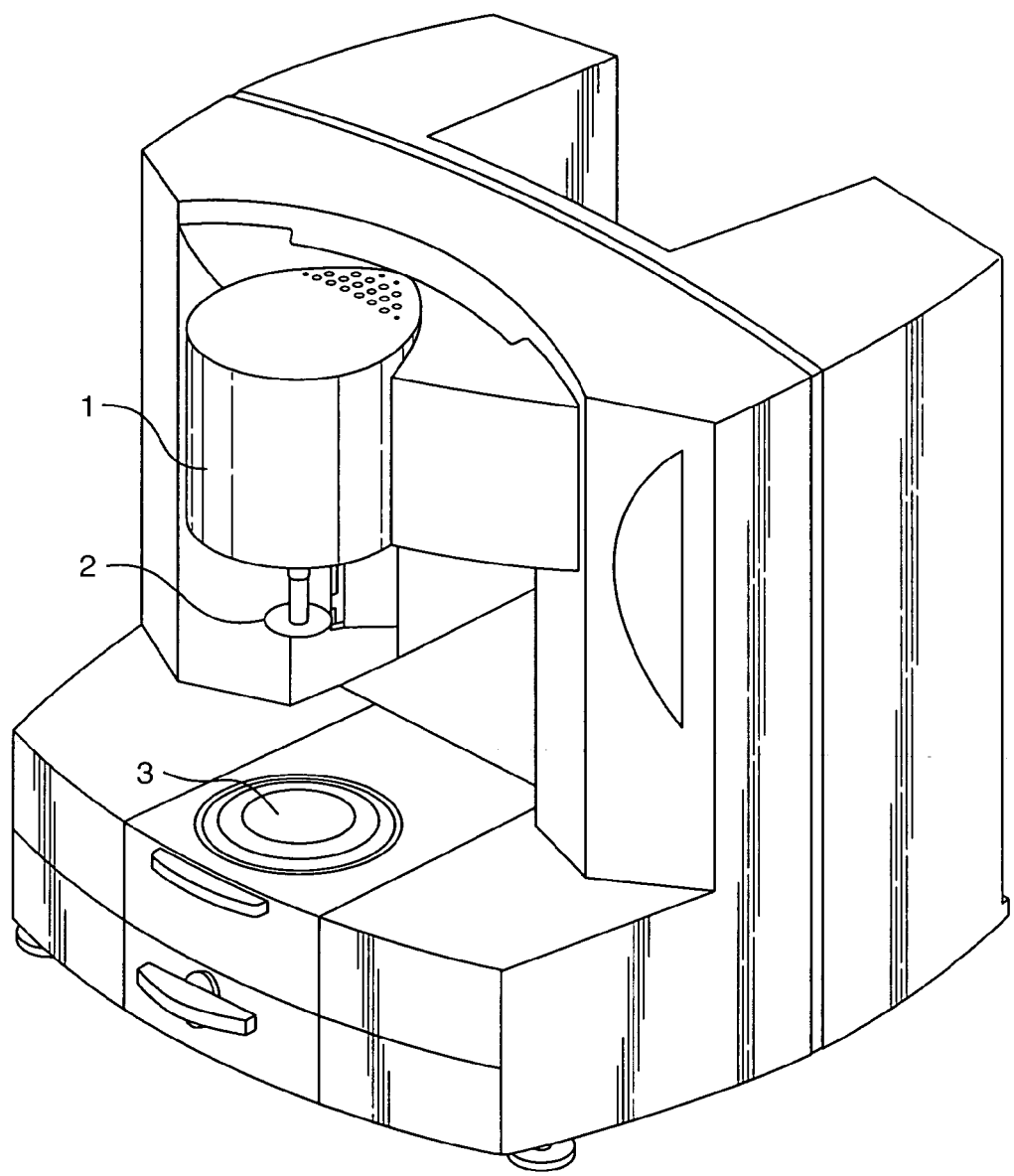
FIG. 1 is a perspective view of a rheometer according to the invention with an environmental control cartridge inserted.

Referring to FIG. 1, an illustrative rheometer according to the invention includes a chassis that holds a head 1, an upper part 2, and a lower part 3. The lower part is mounted on top of a replaceable environmental control cartridge. In this embodiment, the environmental control cartridge slides into the chassis horizontally from the front of the instrument. Other orientations could also be provided for, however, such as one in which the cartridge slides downwardly.

Figure 2:
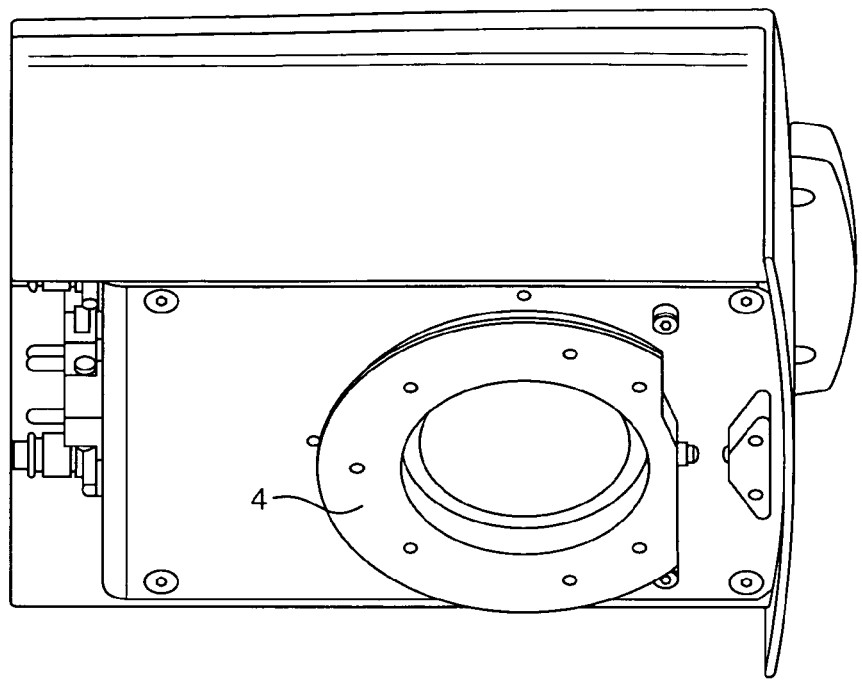
FIG. 2 is a perspective view of an environmental control cartridge for the rheometer of FIG. 1 viewed from the bottom of the cartridge.

Referring to FIG. 2, the cartridge is it generally drawer-shaped with a handle on the front, ports on the back, and an alignment portion 4 on the bottom. In this embodiment, the alignment portion includes a dovetailed disc. One of ordinary skill in the art will recognize, however, that other types of alignment mechanisms could be used, and they can be positioned on different parts of the cartridge and/or chassis.

Figure 3:
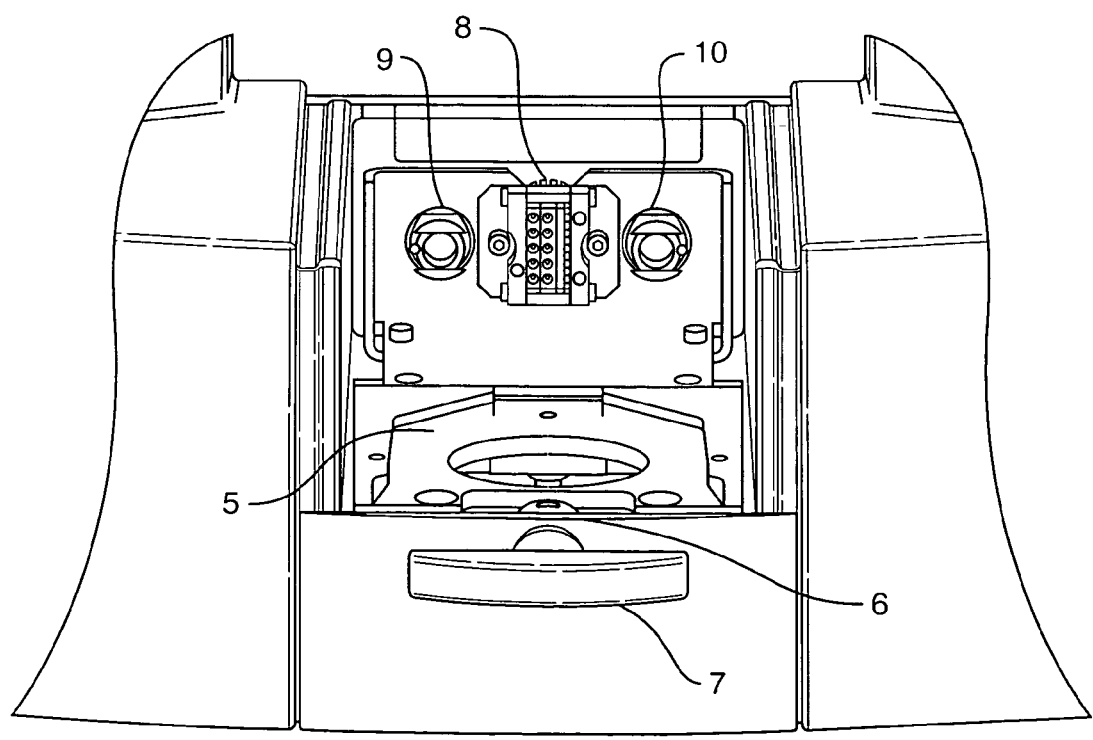
FIG. 3 is a plan view of a lower portion of the rheometer of FIG. 1 with its environmental control cartridge removed to show its environmental Control cartridge interface.

Referring to FIG. 3, the alignment portion for the environmental control cartridge interacts with a v-block 5 in the chassis. Electrical parts 8, and fluid ports 9, 10 are provided so that they can interact with corresponding ports on the back of the cartridge. The electrical ports can provide incoming and outgoing signals of a variety of types, such as control signals, sensor signals, or cartridge identification signals. Similarly, the fluid ports can provide incoming and outgoing fluids of a variety of types, such as cooling liquids, pressurization fluids, or gases. A handle 7 is connected to a cam 6 that locks the environmental control cartridge into its aligned position.

Figure 4:
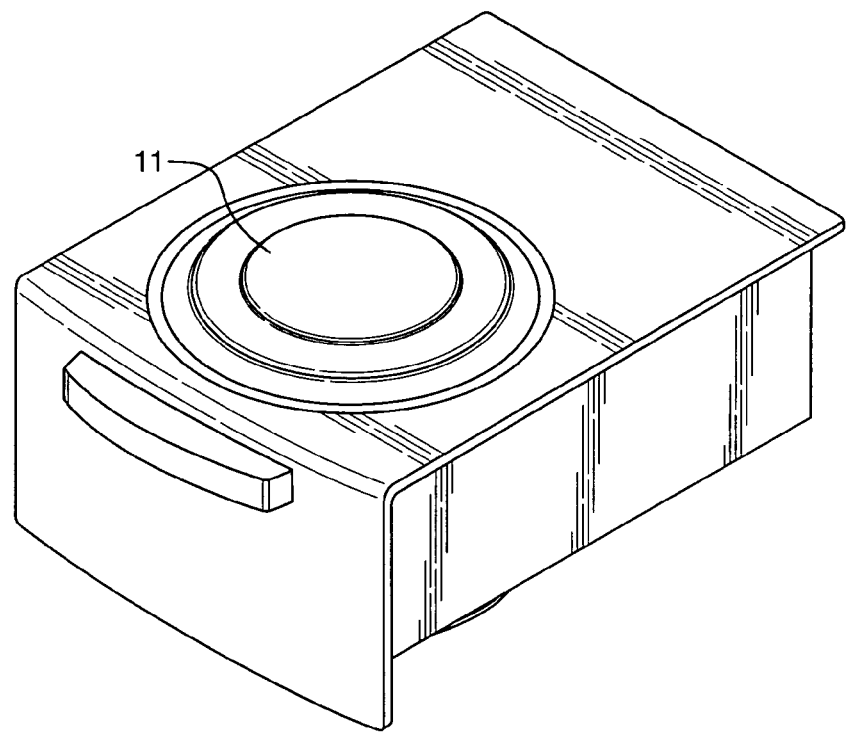
FIG. 4 is a perspective view of the cartridge shown in FIG. 2 viewed from the top.
Figure 5:
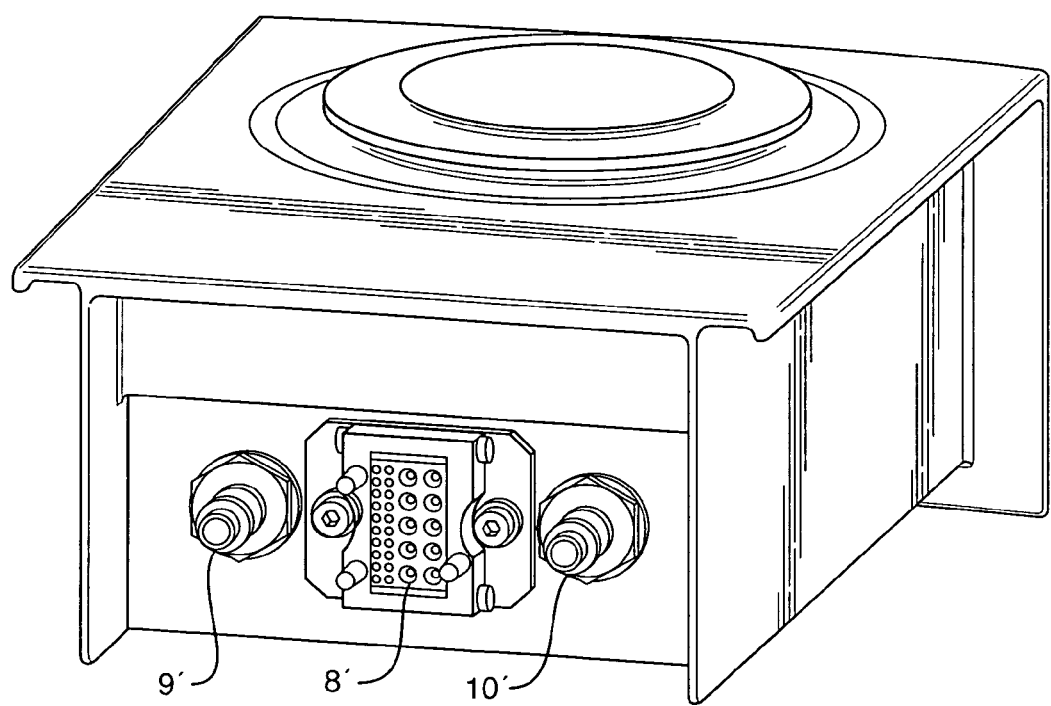
FIG. 5 is a perspective view of the cartridge shown in FIG. 2 viewed from the rear.

Referring to FIGS. 4-5, the ports on the cartridge 8', 9', 10' (on FIG. 5) are designed to meet with corresponding ports on the chassis. In this embodiment, the ports on the chassis are spring loaded and provided with broad alignment pins to allow the ports to engage each other without affecting the alignment of the cartridge.

The rheometer preferably uses a secondary alignment system to allow all cartridges to work in all rheometers in the same product line. In this embodiment, the v-block is adjustable within the chassis of the rheometer. Its position can then be precisely set during manufacturing, so that cartridges that are inserted in any machine are always lined up with respect to the head and top part.

Changing between different environmental controllers tends to be quite difficult in current rheometer instrumentations because many factors should be considered when designing accessories. There are competing elements involved in designing environmental controllers for rheometers and implementing a plug and play strategy. The mechanical alignment should be independent of any other connections in order to make it repeatable to the levels that are required by rheometers. Any electrical or fluid connectors also need to have reproducible and reliable connections to the instrument which aren't affected by the alignment of the sample measurement geometries that are present. The two systems—mechanical alignment for rheology and provision of services to the controller need to be isolated from each other in a way that allows them both to work effectively and reproducibly within the same cartridge.

Alignment between the rheometer head, geometry and environmental controller (FIG. 1, parts 1, 2 and 3 respectively) is crucial for good rheology. Misalignment will result in wrong or inconsistent rheological data. For this reason, the alignment for each environmental cartridge is entirely self-contained. The cartridge is aligned internally to make sure that the dovetail (FIG. 2, part 4) and the measurement surface (FIG. 4, part 11) are aligned to an accuracy appropriate for rheology. The dovetail fits into the v-block of the instrument (FIG. 3, part 5), which is itself aligned with the head (FIG. 1, part 1). Consequently each environmental cartridge will have appropriate alignment built-in. This means that new environmental controllers, or swapping of environmental controllers will not require lengthy realignment on the instrument.

The cartridges use a simple interface with the customer to make sure that the alignment is accurate; the dovetail is forced into the v-block with a known force using a cam mechanism which is operated by a handle (FIG. 3, parts 6 and 7, respectively). This alignment technique allows a complex set of parts to be simply and reproducibly aligned to any instrument in the same product line.

Rheometer environmental controllers invariably require services to make them function. Usually these are in the form of power, sensing and fluids connection. The new interface uses floating connectors on one side, which interact with fixed connectors on the other side (FIG. 5, parts 8', 9', and 10', and FIG. 3, parts 8, 9 and 10 show the floating connector on the cartridge and a fixed connector on the instrument but this may be reversed). The connections fall into two categories, electrical and fluid. The electrical connectors (FIG. 5, part 8' and FIG. 3, part 8) consist of power circuitry and sensing circuitry (including but not limited to temperature—other examples may be pressure, light, electrical or magnetic parameters). These take power from the instrument to drive the cartridge and measure appropriate outputs from the cartridge to provide the user with information and help control the inputs. The fluids connectors are primarily for use with external (to the instrument) circulators which provide thermal exchange fluids to the cartridge where necessary. The connectors in this embodiment are self-actuating, which means that the user does not have to remember to disconnect or switch off the circulator prior to disconnecting the cartridge.

Integrating the connectors into the cartridge is believed to be novel for rheometers. Many prior art rheometer environmental controllers have a range of electrical and fluid connectors that must be plugged into various places before the environmental controller can function. Sometimes the connectors are on the rear of the instrument, sometimes they are within the instrument body, and usually there is more than one external connection that has to be made with flying leads. The embodiment presented is a step forward from these types of rheometers because all of the connections are made simultaneously, as the cartridge is inserted, making the correct connection easy and safe. The interface is also standardized which enables all cartridges to work from the same, easy to use system. The instrument intelligently detects the presence of a cartridge, or lack thereof and enables and disables the power accordingly, making the connection process safe.

The rheometer of FIG. 1 also uses intelligence technology within the cartridge that informs the instrument what type of environmental controller is connected and what its calibration constants, limits and personality are (this includes configuration information, equilibrium limits and capabilities). The instrument polls the cartridge for this information and can retrieve the details within seconds, to make the cartridges truly hot-swap and plug and play—some prior art rheometers require a restart of the instrument and software to recognize the new environmental controller. The rheometer in this embodiment automatically recognizes that the new controller is present and what its capabilities are, and it will then configure the rest of the instrument accordingly—for example the upper geometry type (FIG. 1, part 2) is dependent on the cartridge type (bobs cannot be used with a plate cartridge configuration, for example).

Example 1

This example illustrates using both cylinder geometries and cone/plate geometries on an instrument.

Many customers have requirements for making measurements using cup and bob geometries (usually for low viscosity fluids or standard specification tests) and also for making measurements with cone and plate or plate/plate geometries (for higher viscosity samples or for dynamic testing using lower inertia geometries). In prior art instrumentation, swapping from a plate controller to a cylinder controller may require the following steps:

1 Remove upper geometry
2 Switch off instrument
3 Close software
4 Undo clamps that hold the plate controller into the instrument
5 Undo any electrical connections to the instrument
6 Undo any fluid connections to the instrument
7 Remove the plate controller
8 Connect any cylinder electrical connections to the instrument
9 Connect any cylinder fluid connections to the instrument
10 Insert the cylinder controller
11 Tighten clamps that hold the cylinder controller into the instrument
12 Power up the instrument
13 Restart software
14 Check for fluid leaks
15 Insert new upper geometry
16 Check alignment of the cylinder controller and adjust as necessary
17 Possibly change the type of controller that the instrument thinks is connected
18 Zero new geometry The steps used for this embodiment of the invention are as follows:

1 Remove upper geometry
2 Turn clamp handle
3 Remove plate cartridge
4 Insert cylinder cartridge
5 Turn clamp handle
6 Insert new geometry
7 Follow instructions to zero new geometry The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A rheometer for measuring properties of a sample, comprising:
   a mobile part having a contact surface for contacting the sample,
   a fixed part having a contact surface for contacting the sample,
   a vertical actuator for providing relative vertical motion between the mobile part and the fixed part,
   a rotary actuator for providing relative rotary motion between the mobile part and the fixed part,
   a chassis operative to support the actuator, and including an environmental control cartridge interface that includes at least one supply port and at least one mechanical alignment interface, and
   a removable integrated environmental control cartridge including at least one environmental control unit, at least one supply port operative to interact with the supply port for the chassis, and at least one mechanical alignment interface operative to interact with the mechanical alignment interface of the chassis to align both the mobile part with respect to the fixed part and the chassis supply port with respect to the environmental control cartridge part.

2. The apparatus of claim 1, wherein the mechanical alignment interface for the chassis, the supply port for the chassis, the mechanical alignment interface for the environmental control cartridge, and the supply port for the environmental control cartridge are positioned to cause the mechanical alignment interfaces and the supply ports to both engage each other, respectively, at substantially a same predetermined cartridge insertion position.

3. The apparatus of claim 1 wherein the at least one supply port is at least one electrical supply port.

4. The apparatus of claim 3 wherein the at least one electrical supply port is operative to supply control signals to and from the integrated environmental control cartridge.

5. The apparatus of claim 3 wherein the at least one electrical supply port is operative to supply identification signals from the integrated environmental control cartridge.

6. The apparatus of claim 3 wherein the at least one electrical supply port is operative to supply electrical power to the integrated environmental control cartridge.

7. The apparatus of claim 3 wherein the at least one electrical supply port is operative to supply control signals to and from the integrated environmental control cartridge, to supply identification signals from the integrated environmental control cartridge, and to supply electrical power to the integrated environmental control cartridge.

8. The apparatus of claim 1 wherein the at least one supply port is at least one fluid circulation port.

9. The apparatus of claim 8 wherein the at least one supply port is at least one environmental fluid circulation port.

10. The apparatus of claim 9 wherein the at least one supply port is a gaseous material circulation port.

11. The apparatus of claim 8 wherein the rheometer further includes a fluid conveyance control device outside of the environmental control cartridge that controls the conveyance of fluid through the fluid supply port of the chassis and further including disabling logic operative to disable the fluid conveyance control device when an integrated environmental control cartridge is removed.

12. The apparatus of claim 1 wherein the at least one supply port is least one compound electrical and cooling supply port.

13. The apparatus of claim 12 wherein electrical and cooling portions of the at least one supply port are positioned on the environmental control cartridge and on the chassis to simultaneously engage with their respective counterparts upon insertion.

14. The apparatus of claim 1 further including hot-swappable control logic operative to allow the integrated environmental control cartridge to be exchanged even while the chassis is powered up.

15. The apparatus of claim 1 wherein the at least one supply port includes at least one self-actuating connector.

16. The apparatus of claim 1 wherein the fixed part is integrated into the integrated environmental control cartridge.

17. The apparatus of claim 16 wherein the at least one mechanical alignment interface is operative to constrain at least a portion of the integrated environmental control cartridge in three dimensions with respect to the moveable part.

18. The apparatus of claim 1 wherein the at least one mechanical alignment interface is operative to constrain at least a portion of the integrated environmental control cartridge in three dimensions with respect to the moveable part.

19. The apparatus of claim 18 wherein the at least one mechanical alignment interface is based on a kinematic alignment mechanism that provides a positioning reproducibility of within about +/− ten microns in all three dimensions.

20. The apparatus of claim 1 wherein the at least one mechanical alignment interface is based on a cam.

21. The apparatus of claim 1 wherein the at least one mechanical alignment interface is based on a dovetailed disk and a v-block.

22. The apparatus of claim 21 wherein the environmental control cartridge is inserted horizontally and the mechanical alignment interfaces are based on a horizontally mounted dovetailed disk and a horizontally mounted v-block.

23. The apparatus of claim 22 wherein a position of the v-block is adjustable to allow the environmental control cartridge's position to be adjusted to a chassis-independent standard position.

24. The apparatus of claim 1 wherein each of the at least one mechanical alignment interface provides for an individual adjustment to allow the environmental control cartridge's position to be adjusted to a chassis-independent standard position.

25. The apparatus of claim 1 wherein each of the at least one alignment interface is a compound interface that provides a first alignment interface portion to align the environmental control cartridge with respect to the mobile part and a second alignment interface portion to align the at least one supply port.

26. The apparatus of claim 25 wherein the second alignment portion includes a loosely sprung mount for the chassis supply port.

27. The apparatus of claim 25 wherein the second alignment portion includes a loosely fitting guide post.

28. A rheometer for measuring properties of a sample, comprising:
a mobile part having a contact surface for contacting the sample,
a fixed part having a contact surface for contacting the sample,
a vertical actuator for providing relative vertical motion between the mobile part and the fixed part,
a rotary actuator for providing relative rotary motion between the mobile part and the fixed part,
a chassis operative to support the actuator, and including an environmental control cartridge interface including at least one cartridge identification interface, and
a removable integrated environmental control cartridge including at least one environmental control unit, and at least one cartridge identification interface operative to report an identity of the integrated environmental control cartridge to the environmental control cartridge identification interface of the chassis.

29. The apparatus of claim 28 wherein the at least one environmental control cartridge identification interface includes one or more electrical connectors.

30. A method of operating a rheometer, comprising:
receiving an environmental control cartridge,
aligning the environmental control cartridge with respect to a mobile part of the rheometer,
aligning a supply port on the environmental control cartridge with respect to a supply port on a chassis of the rheometer, and
engaging the aligned supply ports.

31. The method of claim 30 wherein both of the steps of aligning and the step of engaging all take place substantially simultaneously.

* * * * *